US007553446B1

(12) United States Patent
Treece et al.

(10) Patent No.: US 7,553,446 B1
(45) Date of Patent: Jun. 30, 2009

(54) BIOLOGICAL AGENT DECONTAMINATION SYSTEM AND METHOD

(75) Inventors: Randolph Edward Treece, Westminster, CO (US); Jimmy Ray Smith, Jr., Boulder, CO (US); Douglas W. Swartz, Lakewood, CO (US)

(73) Assignee: Astralux, Inc., Boulder, CO (US)

( * ) Notice: Subject to any disclaimer, the term of this patent is extended or adjusted under 35 U.S.C. 154(b) by 341 days.

(21) Appl. No.: 11/118,610

(22) Filed: Apr. 28, 2005

Related U.S. Application Data

(60) Provisional application No. 60/566,356, filed on Apr. 28, 2004.

(51) Int. Cl.
*A61L 2/08* (2006.01)
*A61L 2/10* (2006.01)

(52) U.S. Cl. ..................... 422/22; 422/24; 250/455.11
(58) Field of Classification Search ..................... None
See application file for complete search history.

(56) References Cited

U.S. PATENT DOCUMENTS

| | | | |
|---|---|---|---|
| 6,699,770 | B2 | 3/2004 | Torvik |
| 6,870,204 | B2 | 3/2005 | Torvik et al. |
| 6,893,932 | B2 | 5/2005 | Torvik et al. |
| 2004/0022665 | A1* | 2/2004 | Lu ................................ 422/1 |
| 2005/0082554 | A1 | 4/2005 | Torvik |
| 2007/0189459 | A1* | 8/2007 | Eaton et al. .................. 378/143 |

FOREIGN PATENT DOCUMENTS

WO WO03039608 A2 * 5/2003

OTHER PUBLICATIONS

Williams, G. R., et al.. Laser action in strongly scattering rare-earth-metal-doped dielectric nanophosphors. Dec. 2001, Physical Review A, v.65, pp. 013807-1 to 013807-6.*
Li, B., et al., Continuous-wave ultraviolet laser action in strongly scattering Nd-doped alumina. Mar. 2002. Optics Letters, Vo. 27, No. 6, pp. 394-396.*
Brand X-ray Tube Co., "X-ray Tube FAQ page," available at http://www.brandx-ray.com/brand_x_ray_tube_co_inc_x_ray_tube_faq_page.htm, 5 pages, prior art.
"UV/X-Ray Bio-Decontamination," Abstract, AF04-004 (undated), 1 page.
"TIAX Awards US Global Nanospace Exclusive License for TIAX Non-Toxic Decontaminant Foam," (Aug. 2003), available at http://www.tiax.biz/aboutus/pdfs/press_releases/decon_foam_0813-03.html, 2 pages.
Whitney, Ellen A., et al., "Inactivation of *Bacillus anthracis* Spores," *Emerging Infectious Diseases*, vol. 9, No. 6 (Jun. 2003), pp. 623-627.
"Volume 1: Annual Report to Congress," Department of Defense Chemical and Biological Defense Program (Apr. 2003), pp. 33-37.
Rotz, Lisa D., et al., "CDC Report Summary: Public Health Assessment of Potential Biological Terrorism Agents," *Emerging Infectious Diseases*, vol. 8, No. 2 (Feb. 2002), pp. 225-230.

Tiron, Roxana, "Decontamination Technology Still Outdated: The Defense Department proposes $52 million for research and development efforts," *National Defense Magazine*, (printed Dec. 29, 2003), available at http://www.nationaldefensemagazine.org/article.cfm?id=1127, 1 page.
"Technology Development," Modec, Inc. Technical Report MOD2003-1012-G (Jun. 3, 2003), pp. 2-8.
All-Clear™ Chem/Bio Decon Foam, USGlobalNanospace, 2 pages at http://www.investorideas.com/Companies/Nanotechnology/Articles/USGlobalNanospace1002,03.asp, and http://216.239.37.104/search?q=cache:3ksn-P_kyOUJ:www.usgn.com/products.htm+All+Clear+chem/bio..., printed Dec. 24, 2003.
"Sandia decontamination foam may be tomorrow's best first response in a chem-bio attack—Sudsy brew neutralizes viral, bacterial, nerve agents in minutes," Sandia National Laboratories, News Releases, (Mar. 1, 1999), available at http://www.sandia_gov/media/cbwfoam.htm, 4 pages.
"Recommended Office Remediation Procedures," EnviroFoam Technologies, Inc. (undated), 5 pages.
"Questions and Answers about Mail Irradiation," prepared by Public Citizen's Critical Mass Energy and Environment Program (updated Apr. 23, 2002), available at www.citizen.org/cmep, pp. 1-8.
Kowalski, W.J., et al., "UVGI Design Basics for Air and Surface Disinfection," *HPAC Engineering* (Jan. 2000), available at http://www.arche.psu.edu/iec/abe/uvhpac.html, 14 pages.
"Ultraviolet Radiation," EPA Guidance Manual Alternative Disinfectants and Oxidants (Apr. 1999), pp. 1-25.
Sonntag, C. von, "The Chemical Basis of Radiation Biology," published Taylor & Francis, Philadelphia , PA, 1987, 1 page (search history).
Sinha, Rajeshwar P., et al., "UV-induced DNA damage and repair: a review," *Photochem. Photobiol. Sci.*, vol. 1 (2002), pp. 225-236.
"Food Irridation," University of Colorado Health Science Center (Dec. 30, 2003), available at http://www.uchsc.edu/pmb/occmed/food.htm, 2 pages.
Vurgaftman, I., et al., "Band parameters for III-V compound semiconductors and their alloys," *J Applied Physics*, vol. 89, No. 11 (Jun. 1, 2001), pp. 5815, 5836, 5847, 5870.
Hirayama, Hideki, et al., "Optical Properties of AlGaN Quantum Well Structures," (undated) 6 pages.
Dingle, R., et al., "Stimulated Emission and Laser Action in Gallium Nitride," *Appl. Phys. Lett.*, vol. 19, No. 1 (Jul. 1, 1971), pp. 5-7.
Wiesmann, D., et al., "Gain spectra and stimulated emission in epitaxial (In,Al) GaN thin films," *Appl. Phys. Lett.*, vol. 69, No. 22 (Nov. 25, 1996), pp. 3384-3386.
"The Decontamination of Anthrax and Other Biological Agents," Hearing before the Comm. on Science (Nov. 8, 2001), available via http://www.house.gov/committees/science, 7 pages.

(Continued)

*Primary Examiner*—Elizabeth L McKane
(74) *Attorney, Agent, or Firm*—Sheridan Ross P.C.

(57) ABSTRACT

A decontamination method is provided that contacts a biologically contaminated object with first radiation having a first wavelength distribution and with second radiation having a second wavelength distribution. The first radiation kills at least most of the microbes on the surface of the contaminated object but not in an interior region of the object. The second radiation kills at least most of the microbes in the interior region of the object.

26 Claims, 8 Drawing Sheets

OTHER PUBLICATIONS

Kowalski et al., "Mathematical Modeling of Ultraviolet Germicidal Irradiation for Air Disinfection," *Quantitative Microbiology*, 2:249-270, 2000.

Kowalski et al., "Effective UVGI System Design through Improved Modeling," 22 pages at http://www.arche.psu.edu/iec/abe/uvmodel.html, Copyright 2000 American Society of Heating, Refrigerating and Air-Conditioning Engineers, Inc.

Kowalski and Bahnfleth, "Immune-Building Technology and Bioterrorism Defense," *HPAC Engineering*, pp. 57-62, 2003.

Brickner et al., "The Application of Ultraviolet Germicidal Irradiation to Control Transmission of Airborne Disease: Bioterrorism Countermeasure," *Public Health Reports* 118:99-114, 2003.

"AISO 11134-2003: Sterilization of health care products—Requirements for validation and routine control—Industrial moist heat sterilization," Product Information, 2 pages at http://www.standards.com.au/select/Script/Details.asp?docn=AS675668837076, printed May 23, 2005.

Sterigenics, "Guidelines for Validation—Radiation Sterlization," Material Evaluation, undated.

Frankenberg et al., "Effectiveness of 1.5 keV aluminum K and 0.3 keV carbon K characteristic X-rays at inducing DNA double-strand breaks in yeast cells," *Int J. Radiat Biol Relat Stud Phys Chem Med*. 50(4):727-41, 1986, Abstract.

Romig, A.D., "Fifty Years of Defending the Nation at Home and Abroad," A Presentation for Materials Solutions Conference/TMS Fall Meeting, Oct. 9, 2002, Sandia National Laboratories, 26 pages.

Yacobi and Holt, "Cathodoluminescence," from Cathedoluminescence Microscopy of Inorganic Solids, ch. 4, pp. 55, 58-59, undated.

Glasser, O., "Physical foundations of radiology," published Harper & Brothers, New York and London, 1944, 1 page (search history).

Gullikson, E., "X-Ray Data Booklet—Section 1.7 Atomic Scattering Factors," 1 page, undated.

Brandt et al., "Hydrogenation of *p*-type gallium nitride," *Appl. Phys. Lett*. 64(17) (1994), pp. 2264-2266.

Vaudo et al., "Characteristics of light-emitting diodes based on GaN *p-n* junctions grown by plasma-assisted molecular beam epitaxy," *J. Appl. Phys*. 79(5) (1996), pp. 2779-2783.

Kowalski, W.J., "Immune building systems technology," (McGraw-Hill, NY eds 2003) p. 346.

List of Published Articles, 1 page at http://www.arche.psu.edu/iec/abe/, printed Jan. 7, 2004.

Molva et al., "Microgun-pumped semiconductor laser," *Appl. Phys. Lett*. 62(8):796-798, 1993.

Hervé et al., "Microgun-pumped blue lasers," *Appl. Phys. Lett*. 67(15):2144-2146, 1995.

Freedonia Group, "Consumer Water & Air Purification Systems—Market Size, Market Share, Demand Forecast, Sales, Company Profiles, Market Research, Industry Trends," 1 page at http://www.freedoniagroup.com/Consumer-Water-And-Air-Purification-Systems.html, published Aug. 2002, printed Dec. 31, 2003.

Sterigenics, "Sterilization Alternatives—Gamma Radiation" 2 pages, undated.

IBA Press release "United States Postal Service® extends its contract with IBA," 1 page, Nov. 7, 2003.

Task 5. Report on the Project—(4) Future Work in Phase II, pp. 18 and 20, undated.

Kuball et al., "Degradation of AlGaN during high-temperature annealing monitored by ultraviolet Raman scattering," *Appl. Phys. Lett*. 74(4):549-551, 1999.

Business Communications Company, Inc. Press Release, published 2003, 3 pages at http://www.bccresearch.com/editors/RB-168.html, printed May 23, 2005.

Wyms, H.D., "2003 DoD Advance Planning Briefing for Industry," Brooks City-Base, Texas, Apr. 9, 2003, 14 pages.

Navy Training System Plan for the Joint Service Sensitive Equipment Decontamination System, N78-NTSP-A-50-0117/I, Apr. 2002, 3 pages.

Jonathan L. Shaw, et al., "Electron Emission From GaN n-p Junctions," Appl. Phys. Lett., 2002, 81, 3076.

Jonathan L. Shaw, et al., "Emission From GaN p-n Junction GaN Diodes," Cold Cathodes II, Proceedings of the Electrochemical Society, (Cahay, K. L. Jensen, P. D. Mumford, V. T. Binh, C. Holland, and J. D. Lee, eds., 2002), pp. 339-350.

R. E. Treece, et al., "Cold Cathode Electron Emitters Made from GaN p-n Diodes," The 7th Wide Bandgap Nitride Workshop Series, Richmond, VA, Mar. 10-14, 2002.

W. Hug, et al., "Deep UV Laser Diode for UV Resonance Enhanced Raman Identification of Biological Agents," IEEE/LEOS Semiconductor Laser Workshop-CLEO Conference, Baltimore, MD, Jun. 6, 2003.

A Bhattacharyya, et al., "Deep UV Stimulated Emission by Electron Beam Pumping of Bulk AlGaN Alloys," The 8th Wide Bandgap Nitride Workshop Series, Richmond, VA, Sep. 29-30, 2003.

Abstract of Awarded Department of Defense Contrast AF 04-004. Entitled "Portable E-beam Pumped UV/X-ray Bio-Decontamination System." Awarded: Apr. 26, 2004. Available at http://www.dodsbir.net/selections/abs041/dodabs041.htm accessed Nov. 3, 2008.

\* cited by examiner

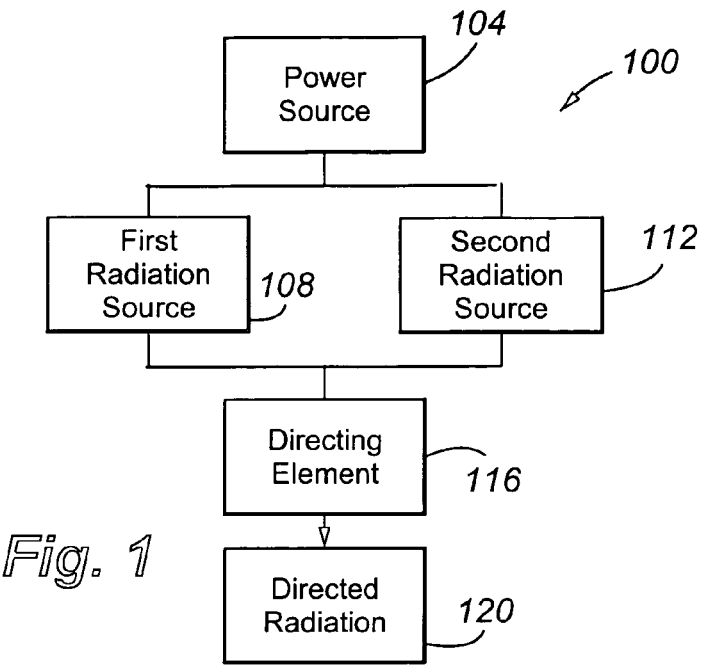
Fig. 1
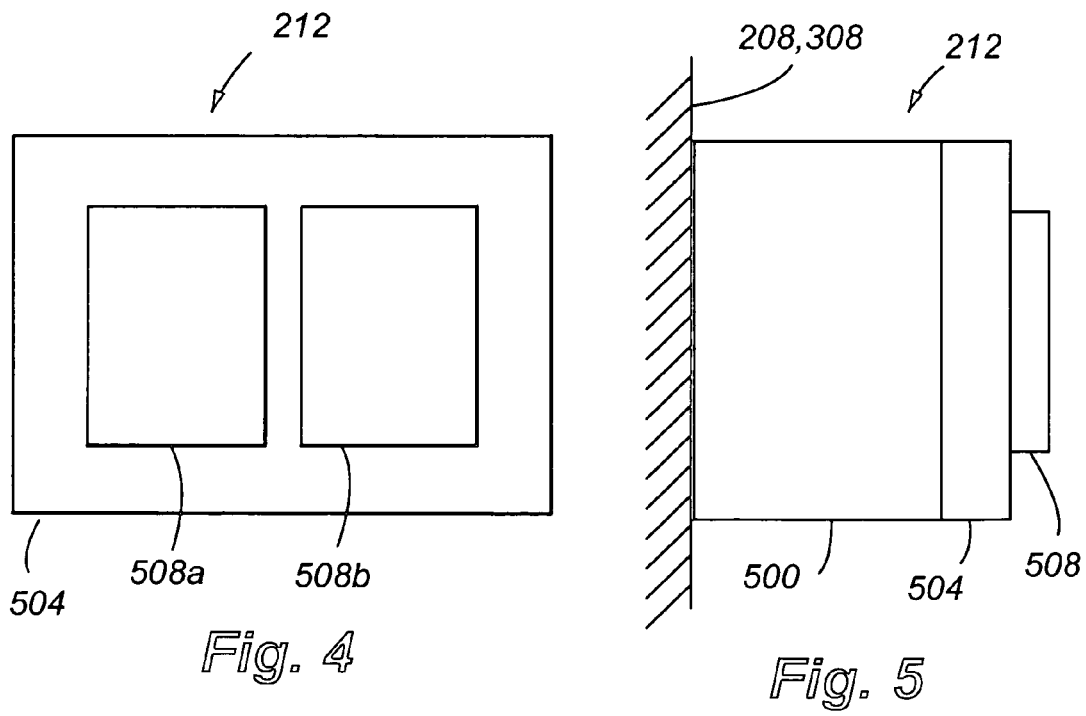
Fig. 4
Fig. 5

BIOLOGICAL AGENT DECONTAMINATION SYSTEM AND METHOD

CROSS REFERENCE TO RELATED APPLICATION

The present application claims the benefits, under 35 U.S.C. §119(e), of U.S. Provisional Application Ser. No. 60/566,356, filed Apr. 28, 2004, having the same title, which is incorporated herein by this reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. FA9451-04-M-0074 awarded by the U.S. Air Force.

FIELD

The invention relates generally to decontamination systems and methods and particularly to biological decontamination systems and methods.

BACKGROUND

Biological weaponry is an increasingly important concern for military and nonmilitary governmental personnel. Since the first World War, the militaries of industrialized nations have been concerned with the use of chemical and biological weapons in global conflicts and more recently by third world "rogue" nations such as Iraq. It is currently estimated that a dozen countries have biological weapon programs. Potential biological warfare agents that can be used in military conflicts include various bacteria, bacterial toxins, viruses, protozoa/parasites, and resistant spore-forming organisms. It is widely anticipated that chemical and biological weapons will be terrorist weapons of choice in the twenty-first century. Such weapons can effect a high civilian death toll and can be difficult to detect. For some biological agents, only a small dosage is required to start an epidemic, and the dosages can be transported long distances through packages and letters while still maintaining their lethality. An example is the effective transportation of *Bacillus Anthracis* spores through the mail during the fall of 2001, which caused 23 human anthrax infections (five of which were fatal). In addition to *Bacillus Anthracis* spores, the U.S. Center for Disease Control and Prevention has identified the agents that cause botulism, plague, smallpox, tularemia, and viral hemorrhagic fevers as the highest priority biological terrorist weapons due to the potential for easy dissemination and high mortality rates.

The U.S. military currently relies on three decontamination agents for neutralizing chemical warfare agents and killing biological warfare agents. The agents are super tropical bleach (or STB), high test hypochlorite (or HTH), and a nonaqueous formulation referred to as decontamination solution number 2 (DS-2). STB and HTH are hazardous materials requiring extreme care during handling, storage, and application. DS-2 is not as corrosive as STB and HTH but does attack paint, plastics, and leather and is not effective in killing spore-form biological warfare agents. Military researchers have been developing non-toxic and non-corrosive decontamination foams based on an enzyme or surfactants/mild oxidizing agents. Although early results are promising for some decontamination applications, the foams can be destructive to paper documents, files, and books and potentially harmful to sensitive military equipment. They require extensive cleanup procedures and equipment after application.

Gas-based decontamination techniques are an alternative to the wet methods currently employed by the military. Candidate gases include chlorine dioxide, hydrogen peroxide, and ozone, among others. However, the efficacy of gas-based techniques is strongly influenced by environmental variables, such as circulation, temperature, and humidity and hence not suitable for outdoor applications. The gases can also be corrosive to some materials. After sterilization, the gases can leave behind persistent toxic vapors in the workspace resulting in health hazards and noxious odors.

Another decontamination technique is irradiation using an electron beam. This technique has been used by the U.S. Postal Service to kill various biological agents while minimizing damage to the mail. The effectiveness of this technique has been questioned due to limited penetration depths. The equipment is also bulky due to the use of large linear electron accelerators.

Finally, ultraviolet (or UV-C) radiation has been used for certain disinfection applications. The technique is known as ultraviolet germicidal irradiation (or UVGI). UVGI has been widely used for disinfecting laboratory and medical equipment since the early 1900s. More recently, it has been used for water purification and has seen limited applications for airstream disinfection.

SUMMARY

These and other needs are addressed by the various embodiments and configurations of the present invention. The present invention is directed generally to the use of various wavelengths of radiation to kill microbes. As used herein, a "microbe" refers to a microscopic or ultramicroscopic organism, such as molds, fungi, viruses, bacteria, protozoa, parasites, and the like.

In one embodiment, a decontamination method is provided that includes:

(a) contacting a biologically contaminated object with first radiation having a first wavelength distribution; and (b) contacting the contaminated object with second radiation having a second different wavelength distribution. The first radiation kills at least most of the microbes on the surface of the contaminated object but not in an interior region of the object, while the second radiation kills at least most of the microbes in the object's interior region. In an exemplary configuration, the first radiation is ultraviolet radiation, and the second radiation is x-ray radiation. Steps (a) and (b) can occur simultaneously or sequentially.

In one configuration, the radiation is produced by contacting a common target with an electron beam to produce simultaneously the first and second radiation. The target includes a first material that, when contacted with the electron beam, produces the first radiation and a second material, that, when contacted with the electron beam, produces second radiation. Preferably, the first material has the formula, $Al_xGa_{1-x}N$, where $0<x<1$, and the second material is a metal.

The combination of a UV emitter and an x-ray emitter can offer a clean, non-toxic, and non-corrosive alternative to conventional decontamination techniques/agents. It can provide high microbe kill rates not only on the surface of a contaminated object but also in interior regions of the object. It can be useful in a wide variety of applications, including mail disinfection, air and water purification, food irradiation, and medical sterilization. It can provide cost savings due to preservation rather than damage or destruction of infected assets and minimization of downtime due to remediation and cleanup. It can provide tuneable peak emission wavelengths that may be tailored to provide optimal kill rates of specific target microbes. It can be implemented in a relatively compact package.

These and other advantages will be apparent from the disclosure of the invention(s) contained herein.

The above-described embodiments and configurations are neither complete nor exhaustive. As will be appreciated, other embodiments of the invention are possible utilizing, alone or in combination, one or more of the features set forth above or described in detail below.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

BRIEF DESCRIPTION OF THE DRAWINGS

FIG. 1 is a block diagram of a biological decontamination system according to the present invention;

FIG. 4 is a plan view of a target according to a third embodiment of the present invention;

FIG. 5 is a side view of the target of FIG. 4;

DETAILED DESCRIPTION

Figure 2:
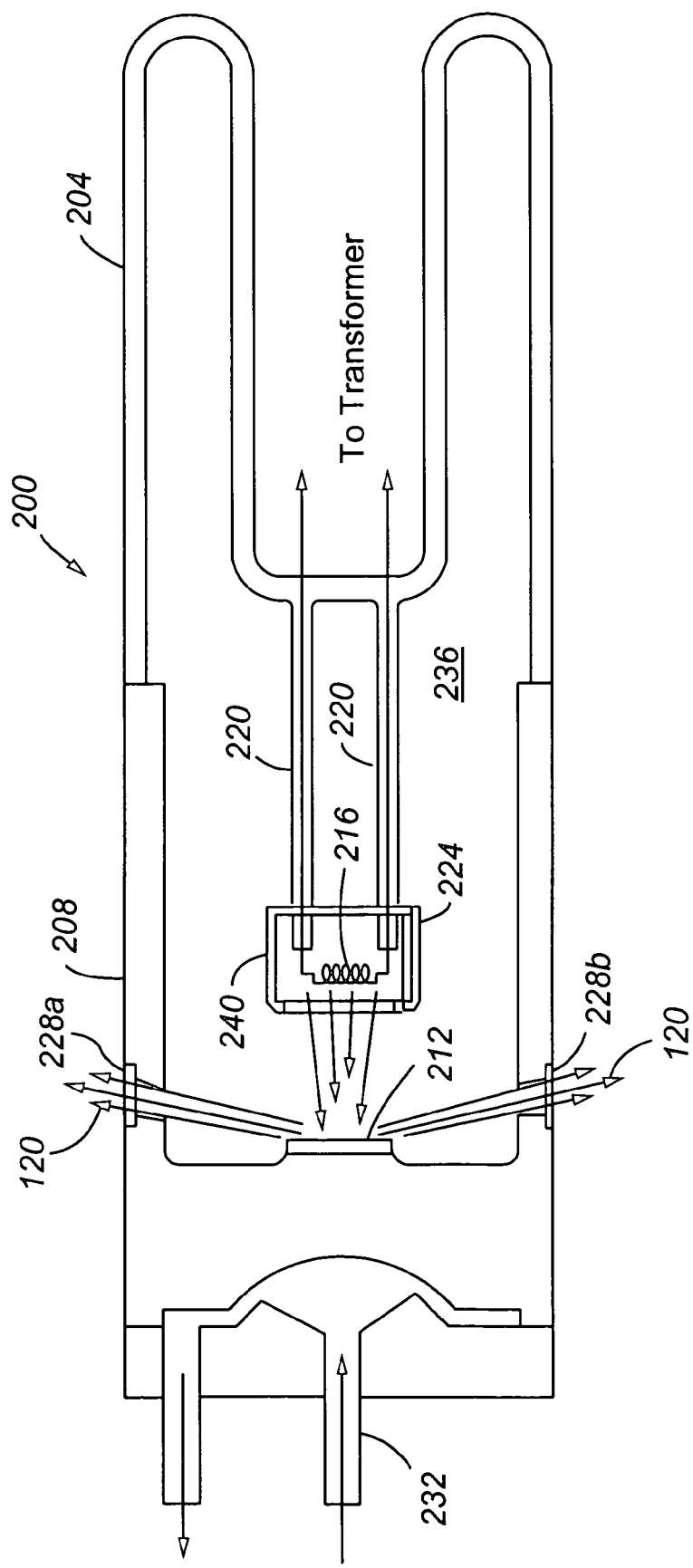
FIG. 2 is a cross-sectional view of an irradiation assembly according to a first embodiment of the present invention.

FIG. 1 depicts a decontamination assembly 100 according to an embodiment of the present invention. The assembly 100 includes a power source 104, first and second radiation sources 108 and 112, and a directing element 116 to provide directed radiation 120. The directed radiation 120 comprises first and second radiation produced by the first and second radiation sources 108 and 112, respectively. The first and second radiation sources 108 and 112 may be the same or different device. For example, the first radiation source can be one or more ultraviolet bulbs while the second radiation source can be one or more x-ray tubes. In this configuration, the first and second radiation sources can be activated simultaneously or alternatively to produce, respectively, first and second radiation simultaneously or sequentially (typically within at least about 10 seconds and more typically within at least about 5 seconds of each source's radiation emission cycle). Alternatively, the first and second radiation can be coproduced within the same device by electron beam excitation of one or more targets. In general, the radiation sources can be any suitable device for producing the first and/or second radiation.

The first radiation has a first wavelength band (or first center wavelength, or first wavelength of maximum emission, $\lambda_{max}$) that is efficacious in killing a first type of microbe and/or killing a broad spectrum of microbes on a surface of an irradiated object while the second radiation has a second wavelength band (or second center wavelength, or second wavelength of maximum emission, $\lambda_{max}$) that is efficacious in killing a second different type of microbe and/or killing a broad spectrum of microbes located below the surface of an irradiated object. The first and second wavelength ranges are typically non-overlapping such that the first and second wavelength bands, first and second center wavelengths, and first and second wavelengths of maximum emission, $\lambda_{max}$, are different from one another.

In one configuration, the first radiation is in the ultraviolet region of the electromagnetic (EM) spectrum while the second radiation is in the X-ray region of the EM spectrum. UV-C radiation sterilizes microorganisms by breaking the hydrogen bond between base pairs in the DNA or RNA, which results in the formation of dimers between pyrimidine molecules. The damage to the DNA and RNA then results in mutagenic changes or cell death. The microorganism is then unable to metabolize or reproduce and therefore cannot cause disease. UV-C radiation, like electron beams, is effective only for surface contaminants because UV-C radiation does not penetrate most substances including dust. X-ray radiation sterilizes microorganisms via photon collisions with the molecules inside a material, which are believed to create a cascade of secondary particles including electrons, ion pairs, and free radicals (especially hydrogen and hydroxyl radicals from water). The secondary particles then initiate chemistry that disrupts the cell DNA in the microbe. The first radiation preferably has a first center wavelength or $\lambda_{max}$ in the range of about 200 to about 400 nm and more typically in the range of about 250 to about 280 nm while the second radiation preferably has a second median wavelength or $\lambda_{max}$ in the range of from about 0.01 to about 10 nm and more typically in the range of from about 0.02 to about 0.2 nm. UV radiation is efficacious for killing surface microbes while the X-ray radiation is efficacious for killing subsurface microbes.

The radiation dose is preferably sufficient to produce at least a 1-log kill in the irradiated biological contaminant. To realize this kill level, the dose typically is at least about 2,000 $\mu J/cm^2$ and more typically at least about 10,000 $\mu J/cm^2$ for the UV radiation component and at least about 0.3 kGy and even more typically at least about 1 kGy for the x-ray or gamma radiation component.

The directing element 116 can be any device for focusing or otherwise directing the radiation to a desired point or area or providing a desired spot size of the radiation on the area. For example, the directing element 116 can be a reflective, refractive, diffractive, diffusive, collimating, or focusing device (such as a lens), and the like.

The size of the power source 104 can be important to the efficacy of the assembly 100. Preferably, the power source ranges from about 30 to about 60 kilovolts.

An assembly 200 according to a one embodiment is shown in FIG. 2. The assembly includes a tubular front housing 204 (which is preferably glass), a tubular rear housing 208 (which is preferably a reflective and conductive material having high thermal conductivity such as copper), a target 212 positioned on the rear housing 208, a filament 216 (which is preferably a metal such as tungsten), power leads 220 to the power source 104, a focusing cup 224, and windows 228a,b (which are preferably a highly UV and X-ray transmissive material such as Schott glass type No. 8337B). The rear housing 208 includes a cooling channel 232 for a heat exchange medium, such as water, to remove heat generated during electron beam excitation of the target 212. To allow electron excitation, the area 236 enclosed by the housing is preferably under vacuum.

In operation, electrical energy is imparted to the filament 216 exciting electrons in the filament with sufficient energy so that they become part of the electron beam 240. The focusing cup 224 and filament 216 act as a negative electrode, which repels and propels the free electrons, in the form of the electron beam 240, towards the positive electrode. The positive electrode or anode is formed by the target 212 and rear housing 208. The anode, being positively charged, attracts the free electrons, accelerating the electrons across the electric field existing between the anode and cathode. This acts to increase the velocity of the electrons, building potential energy. The higher the peak kilovolt rating, the greater the speed at which electrons are propelled across the gap between the cathode and anode. The electrons impact the target 212, releasing potential energy built up by the acceleration of the electrons in the beam. Depending upon the target material that is impacted and the potential energy of the electrons, photons in the ultraviolet or x-ray wavelength spectrum are emitted from the target, forming the directed radiation 120. As will be appreciated, the radiation is the result of excitation of an electron from the valence band to the conduction band within the target due to the energy imparted by electron beam pumping and the subsequent electron relaxation via emission of a photon. Most of the energy from the electrons is converted to heat and is radiated to the rear housing 208 and removed by the thermal exchange medium. The electron beam parameters depend on a number of considerations, including the specific cathodoluminescence material and x-ray generating material, the material thicknesses, UV and x-ray stimulated emission thresholds, desired angular distribution of UV and x-ray radiation, and heating. Desirably, the mean electron beam penetration depth and target material thickness are substantially similar. Preferably to provide adequate levels of fluence, the electron beam excitation ranges from about 10 to about 500 mA and more preferably from about 20 to about 200 mA and from about 10 to about 100 kV and more preferably from about 30 to about 60 kV. As will be appreciated, higher voltages will allow larger excitation volume, increasing output power. Higher current also increases the output power due to increased rate of electron-hole pair generation within the material.

The vacuum in the enclosed area 236 allows for gases and other impurities to be pumped out of the tube, creating the vacuum necessary to avoid disruption of the electron beam and consequent interference with the performance in the UV-C and x-ray radiation process. The vacuum also provides for proper filament performance and durability.

Various cathodes may be used to provide electron excitation of the first and second wavelength bands. These cathodes include, but are not limited to, refractory metal filaments, barium oxide cathodes, carbon nanotubes, diamond nanotips, carbon velvet emitters, semiconductor cathodes, field emission arrays, negative electron affinity cathodes, planar cathodes, and large-area emitters. Inclusion of various cathodes within the device may lead to various embodiments of the device.

Figure 3:
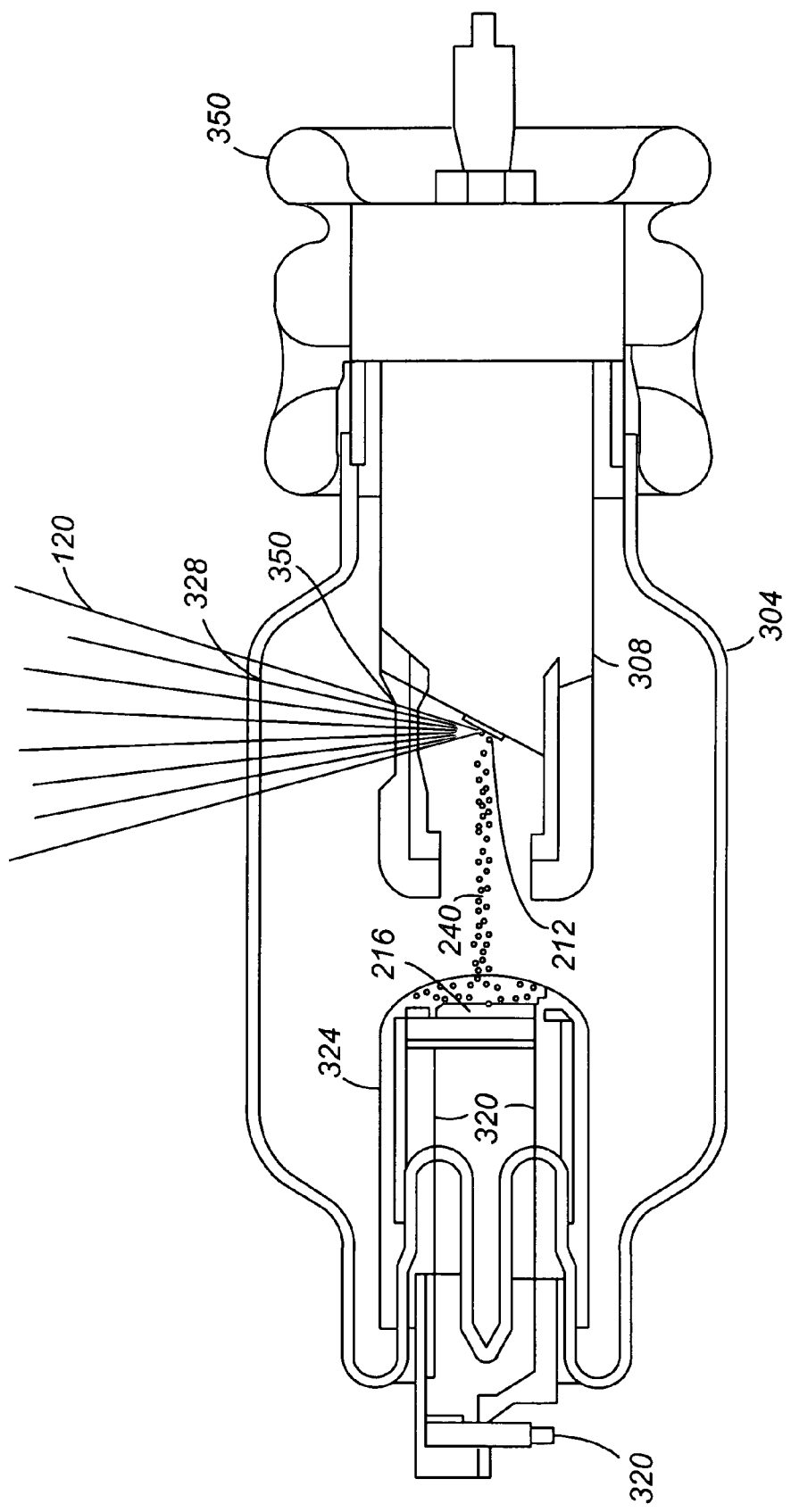
FIG. 3 is a cross-sectional view of an irradiation assembly according to a second embodiment of the present invention.

FIG. 3 shows an assembly 300 according to another embodiment of the present invention. The assembly 300 includes the tubular front housing 304, tubular rear housing 308, target 312 positioned on the rear housing 308, filament 316, a first optically transmissive window 350, power leads 320 to the power source 104, focusing cup 324, and second optically transmissive window 328. The rear housing 208 includes cooling fins 350 to dissipate heat generated during electron beam excitation of the target 212.

FIGS. 4-5 show a target 212 according to an embodiment of the present invention. The target includes a substrate 500 mounted on the rear housing 208, 308, a wide bandgap cathodoluminescent semiconductor material 504 to produce UV radiation, and an x-ray generating material 508 to produce x-ray radiation.

The substrate is preferably monocrystalline and more preferably provides desired characteristics for epitaxial growth of the wide bandgap semiconductor material 504. Preferably, the lattice mismatch between the substrate 500 and material 504 is no more than about 8%. Preferred substrates include sapphire, silicon carbide, aluminum nitride, gallium nitride, and $Al_xGa_{1-x}N$. For better lattice matching, the substrate may include one or more buffer layers positioned adjacent to the material 504.

The material 504 can be any wide bandgap material. Preferably, the material has a gain coefficient ranging from about 10 to about 100 cm$^{-1}$. $Al_xGa_{1-x}N$ (where $0 \leq x \leq 1$) is particularly preferred. High gain coefficients can be achieved by the combination of long range ordering within the lattice and filling of point-defect sites via silicon or indium doping.

The peak emission wavelength is tuneable to enhance the specific damage mechanism, such as RNA or DNA sequence disruption or cell wall damage, thereby allowing optimum destruction of species that are difficult to kill. As will be appreciated, Vegard's law describes the change in bandgap as a function of Al/Ga ratio in the $Al_xGa_{1-x}N$ alloy system. The bandgap measured in cathodoluminescent emission spectra typically corresponds to radiative relaxation from near-band edge excitonic states, which arise from the electron-hole pairs generated by electron impact. By properly choosing the alloy composition, the $Al_xGa_{1-x}N$ material can be adjusted to provide a band of about 50 and more preferably of about 25 nm in width centered around 265 nm, which has been found to be the most potent wavelength for damaging DNA and RNA for many biological agents through the formation of cyclobutane-pyrimidine dimers. To realize this band, it is preferred that x in the formula $Al_xGa_{1-x}N$ be selected such that $0.6 \leq x \leq 0.8$. The material 504 can be a thin film, thick film, or bulk material. Preferably, the material 504 is a thin film material grown on the substrate 500 using molecular beam epitaxy, organometallic chemical vapor deposition, hydride vapor phase epitaxy, or other epitaxial growth techniques. The thickness of the material 508 preferably ranges from about 0.2 to about 5 μm.

The x-ray generating material 508 is preferably a material having the following characteristics: (a) high atomic number, (b) high melting point, (c) high thermal conductivity, (d) low vapor pressure at high temperatures, (e) low cost, and (f) ease of deposition by evaporative techniques. As atomic number increases the intensity and energy of the x-rays increase too. As the atomic number increases, however, the voltage necessary to excite the K and L radiations increases as well. For an excitation beam of about 30 keV electrons, the x-ray generating material 508 preferably has an atomic number (Z) less than about 50 for production of the $K\alpha_1$ emission line, which is the most intense radiation for the K and L emission series. Preferred metals include Al, Cu, Mo, W, and Ag. However, due to heating from the electron beam impact it is also desirable to select a metal with a high thermal conductivity to allow efficient conduction of heat away from the target 212 toward a cooled heat sink. Therefore, silver, with a thermal conductivity of about 4.29 W/cmK, or tungsten, with a thermal conductivity of about 1.74 W/cmK, are the most preferred metals. The thickness of the material 508 preferably ranges from about 0.2 to about 5 µm.

As will be appreciated, the relative proportions of UV and X-ray radiation produced by the target depends on the relative surface areas of the two materials exposed on the irradiated surface of the target. The higher the surface area of the material 508, the greater the proportion of X-ray radiation and the higher the surface area of the material 504, the greater the proportion of UV radiation.

Figure 6:
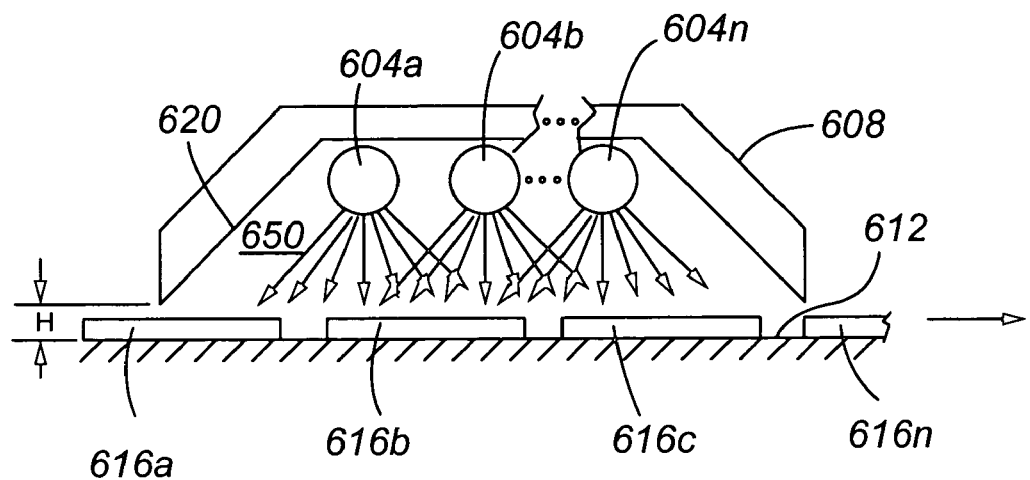
FIG. 6 is a cross sectional view of a decontamination system of an embodiment of the present invention.

FIG. 6 is a configuration of a contamination system according to an embodiment of the present invention. The system includes a plurality of radiation emitters 604*a-n* positioned within a hood 608. The hood 608 is in turn positioned above a moving surface 612 carrying a plurality of objects 616*a-n*, such as envelopes, packages, and luggage. The surface 612 is preferably a continuous web, such as a conveyor belt. The emitters 604 may be any suitable emitters, such as sequenced discrete UV and x-ray emitters and/or co-emitters able to emit both UV and x-ray radiation. The interior surface 620 of the hood 608 is preferably reflective so as to direct the radiation towards the surface 612. The height "H" of the edge of the hood 608 above the surface 612 is preferably high enough to receive the objects but not too high to allow substantial amounts of radiation to escape into the exterior environment. In one configuration, a flap may be rotationally mounted on or near the edges of hood 608 to permit the passage of objects but inhibit the escape of radiation. The flap may be, for example, a radiation reflective or adsorptive surface. The surface 612 is preferably radiation adsorptive and/or diffusive to further limit the amount of radiation escaping into the ambient environment. Preferably, the surface 612 has a mass absorption coefficient of at least about 100 cm$^2$/g. In one configuration, the surface 612 is formed by a number of rotatably connected metal plates, with lead being preferred. As the objects 616 pass beneath the hood and through the irradiation zone 650, microbes on the surfaces of the objects and within the objects are killed synergistically by the combined effects of the UV and x-ray radiation.

Although the system of FIG. 6 is not portable, it is to be understood that the concepts of the present invention can be implemented in a portable unit for decontaminating stationary or immovable objects.

Figures 7, 8:
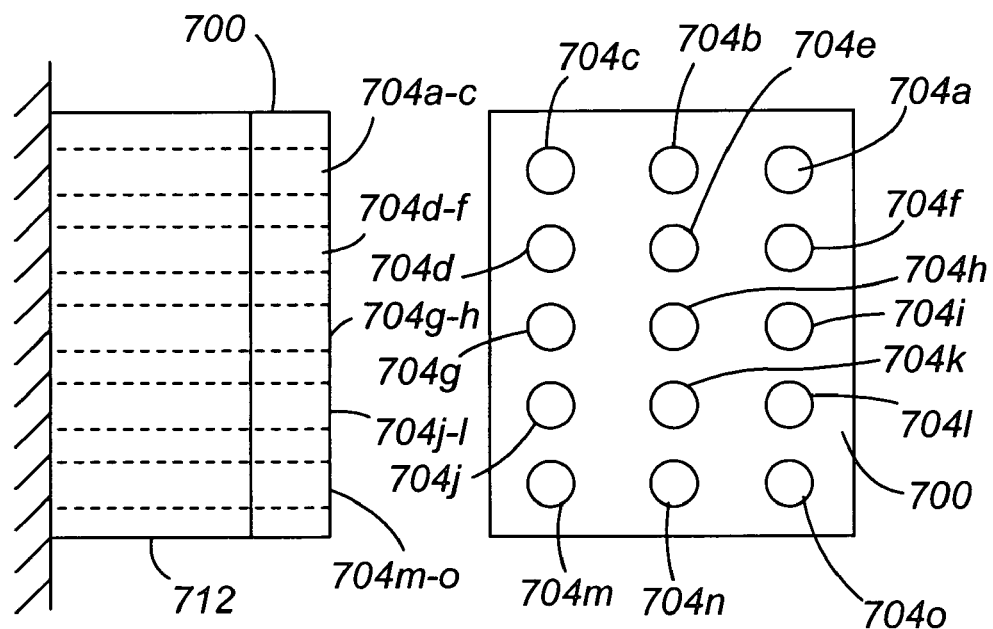
FIG. 7 is a plan view of a target according to a fourth embodiment of the present invention.
FIG. 8 is a side view of the target of FIG. 7.

FIGS. 7-8 depict a target 212 according to another embodiment of the invention. The target includes the cathodoluminescent material 700 with a plurality of x-ray producing elements 704*a-o* of the x-ray producing material. The elements 704*a-o* can be any shape, whether cylindrical (as shown) or angular (e.g., polygonal). The elements 704*a-o* pass through the material 700 and substrate 712 and contact the housing 208, 308. The elements 704*a-o* provide a thermal conduction path to the housing for effective removal of heat generated during radiation emission. As will be appreciated, the elements can alternatively pass through only the material 700 and not the substrate 712 provided that the substrate 712 has a sufficient coefficient of thermal conduction to remove generated heat at an acceptable rate. Alternatively, the x-ray producing material can be substituted for the cathodoluminescent material 700 and the material 700 for the x-ray producing material in the elements 704. The target may be formed by first forming the material 700 on the substrate 712, such as by molecular beam epitaxy, organometallic chemical vapor deposition, hydride vapor phase epitaxy, or another epitaxial growth technique, followed by forming vias through the material (such as mechanical, laser drilling, or etching) and optionally substrate in the locations of the elements, and finally depositing the x-ray producing material in the vias by known techniques, such as chemical vapor deposition or evaporative techniques.

EXPERIMENTAL

Applicants performed a number of tests with $Al_xGa_{1-x}N$ cathodoluminescent materials. A first material was formed having 87% aluminum, a second material having 64% aluminum, and a third material having 70% aluminum. An electron beam was then pumped into the material and UV-C spectra measured. The materials were bulk (uniform layer composition) structures deposited as 1 µm thick active layers on sapphire substrates.

Figure 9:
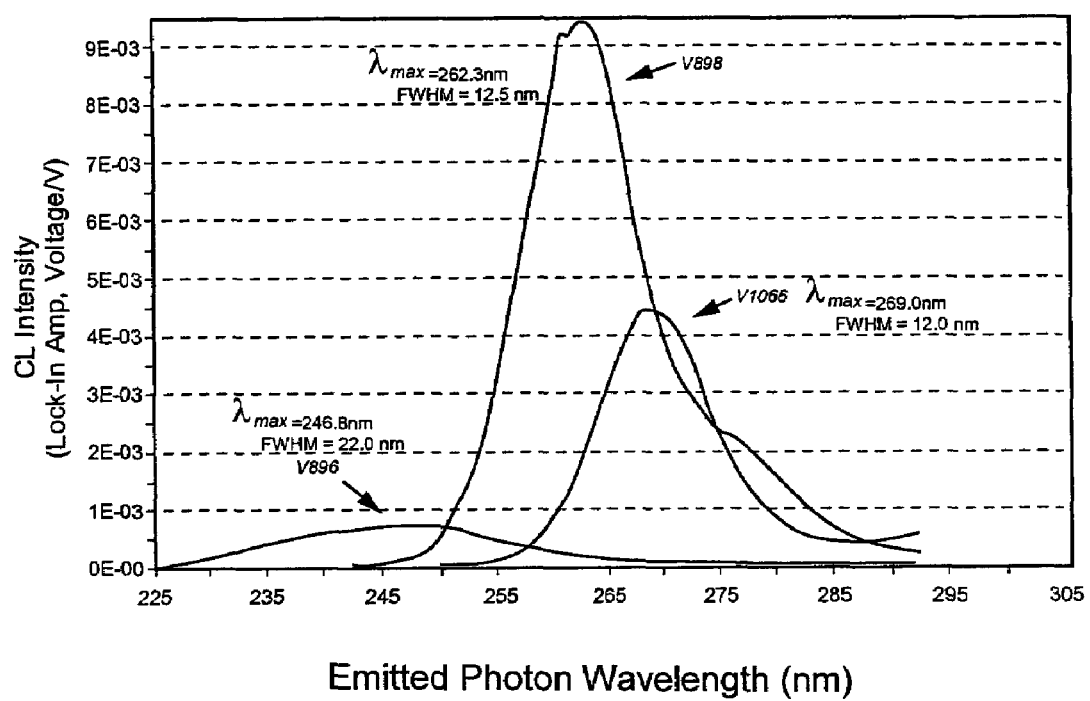
FIG. 9 is a plot of cathodoluminescence (CL) intensity versus emitted photon wavelength for three bulk $Al_xGa_{1-x}N$ films with different Al mole fractions.

The results are shown in FIG. 9. As can be seen from FIG. 9, the first material (sample V896) produced UV radiation having a $\lambda_{max}$ of about 246.8 nm and a FWHM of about 22.0 nm, the second material (sample V1066) UV radiation having a $\lambda_{max}$ of about 269 nm and a FWHM of about 12.0 nm, and the third material UV radiation having a $\lambda_{max}$ of about 262.3 nm and a FWHM of about 12.5 nm. The emission bands of the second and third materials is suitable for germicidal radiation. This experiment illustrates that UV radiation characteristics may be tuned by varying the composition of a cathodoluminescent material.

A vacuum chamber was constructed that allowed both detailed UV characterization and demonstration of x-ray production. A 6-way cross with 4.5 inch flanges was used for the central chamber. Two of the ports had fused silica windows installed for viewing and emission output. In the interior of the cross, a drop-in x-ray scintillator screen (Gadox or $Gd_2O_2S$:Tb layer coated on a glass optic with a 150 nm Al overlayer on top of the layer to bleed charge when the screen is used for the alternate application of electron beam visualization) was positioned. In line with one window, a collection and focusing lens was positioned to focus the radiation on a suitably positioned UV-grating spectrometer. The large diameter view ports permitted easy observation of the electron beam target in vacuum. The sample (or target) was positioned on the end of a linear/rotary stage feedthough mounted in the cross. The chamber was connected to a turbo pump that pumped the chamber to $\sim 1\times10^{-6}$ torr to allow operation of the electron gun.

The electron gun was a low-energy research grade gun from Thermionics (Model VE-052). It has electron energy and filament emission current ranges of 0-20 keV and 0-40 µA, respectively. The actual currents incident on the target mounted in the center of the chamber are significantly lower than the filament emission, namely on the order of 1-100 nA as measured with a Faraday cup, apparently due to significant attenuation or loss of the beam as it travels through the electron optics and into the test chamber.

To test the x-ray detection capability of the chamber, a copper foil target was mounted in the chamber. Copper foil was chosen because it has a relatively low energy absorption edge for x-ray emission. However, it is preferred to use a higher Z metal to generate harder x-ray radiation. Upon bombardment of the target with 10 keV electrons, diffuse, moderately bright green luminescence was observed on the screen. A disadvantage of using the Scintillator screen for x-ray detection is that it responded to UV radiation as well as x-rays, thereby preventing discrimination and confirmation of the presence of both types of radiation.

Figure 10:
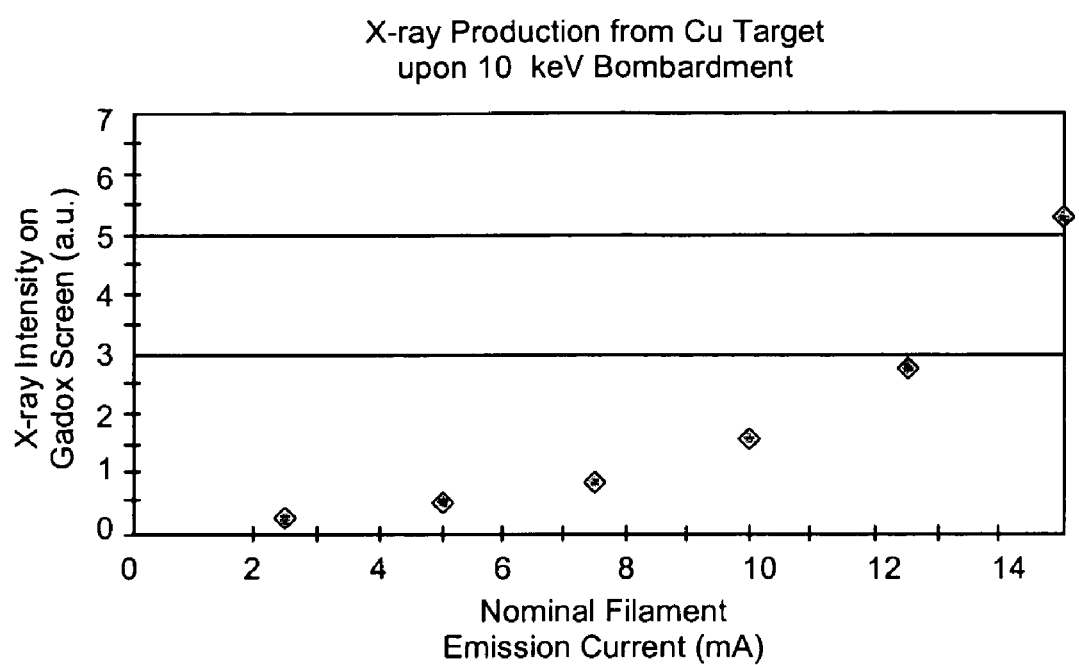
FIG. 10 is a plot of X-ray intensity versus nominal filament emission current.

The intensity of the 545 nm emission from the scintillator screen as a function of ebeam emission current was measured using a PMT detector and lock-in amplifier. FIG. 10 is a plot of this data. The plot demonstrates that the scintillator screen can be used to measure relative x-ray intensities. The nominal filament emission is measured indirectly via the gun power supply. The nonlinear increase in x-ray signal is due to a nonlinear increase in electron current reaching the target, as confirmed indirectly via earlier cathodoluminescence measurements and direct Faraday cup measurements.

The UV-response characteristics of the scintillator screen were determined next. The responses of the screen to both 325 nm laser radiation from a HeCd laser and UV-C emission from a GRINSCH AlGaN sample were tested. A weak, non-uniform response to UV despite the Al coating of the screen was noted. To prevent any screen response to UV, a Be metal foil was used to act as a UV blocking filter in front of the screen.

Next, a target was made having the configuration of FIGS. 4-5 with the x-ray producing material 508 being copper foil and the cathodoluminescent material 504 being $Al_xGa_{1-x}N$. This target was produced in the following manner: A wedge-shaped sample of bulk $Al_{0.72}Ga_{0.28}N$ (approx 8 mm radius) on a sapphire substrate was patterned using a comb photomask and negative-polarity liftoff photoresist. After the photolithography, copper was thermally evaporated on the sample to a thickness of about 330 nm, which is reasonably close to the penetration range of 10 keV electrons within copper. After liftoff, an alternating comb pattern of metal fingers and UV-emitting regions is produced having 50% metal coverage.

The metallized dual emitter sample was then mounted in the test chamber on the end of the linear/rotary feedthrough using silver paste. The sample was then tested for electron beam co-production of UV-C and x-ray radiation using the steps described above. The electron beam incidence on the sample was set to 45°. First, cathodoluminescence (CL) spectra of the sample was measured without the drop-in scintillator x-ray detector. Then, the vacuum chamber was vented and the scintillator screen was put in place. The intensity of the scintillator glow in response to x-rays generated from the target was then measured using the spectrometer.

Figure 11:
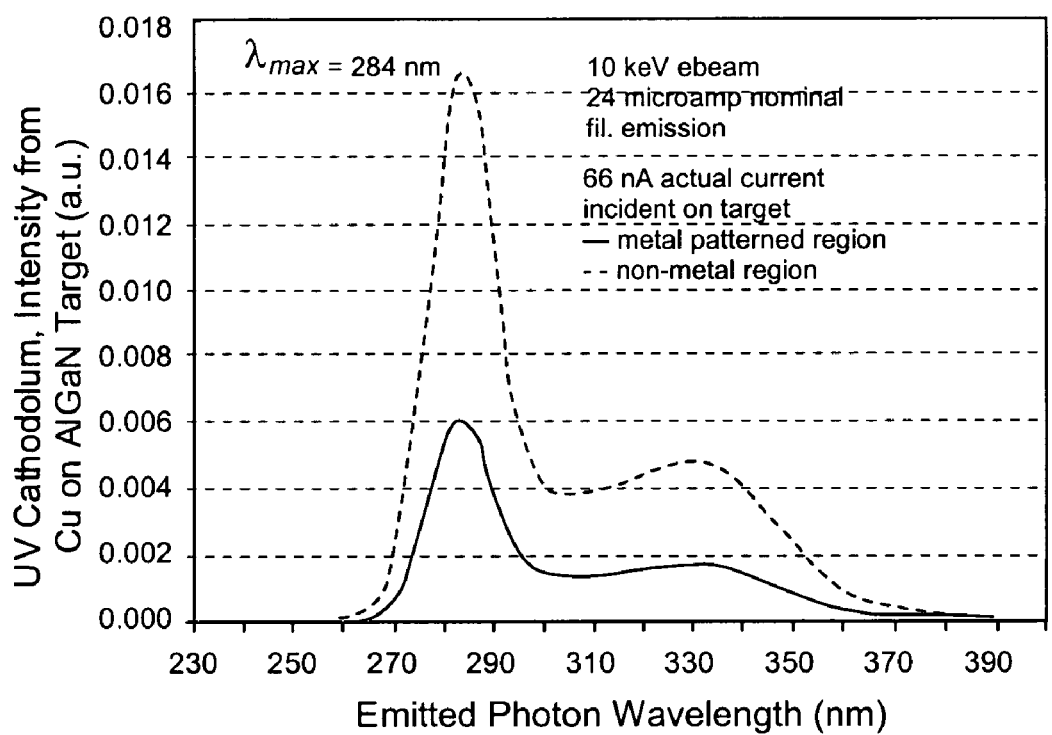
FIG. 11 is a plot of UV cathodoluminescence intensity versus emitted photon wavelength.

FIG. 11 shows the UV CL spectra for two different regions on the sample. The emission was excited using a 10 keV electron beam with 24 µA nominal filament emission current and only 66 nA incident on target, as measured with a Faraday cup. A strong emission band at 284 nm was observed which arises from band-gap luminescence. This is a useful band for UV germicidal irradiation. Weaker sub-bandgap luminescence is observed centered at 332 nm, which arises from chemical or structural impurities in the $Al_{0.72}Ga_{0.28}N$ material. The CL spectrum of the metal patterned region was obtained from a 3×3 mm comb square using electron beam spot diameter which was set to roughly 3 mm diameter. The CL spectrum of the non-metallized region was obtained from a thin non-metallized area at the edge of the sample using the minimum electron beam spot for the electron gun (nominally ~100 µm diameter). The CL intensity from the metal-patterned region is lower than the non-metallized region but still easily measurable with the system. In short, the measured spectra provide definitive evidence of UV emission from the sample.

The final setup for detection of x-ray production used a 1.3 inch diameter and 0.010 inch thick beryllium foil to block the UV from reaching the scintillator screen while allowing x-rays to pass. Silver paste was used to attach the beryllium foil to the circular brass mount used to hold the scintillator screen. The scintillator screen was 40 mm in diameter, so commercial aluminum foil was used to cover the lower half of the screen. Any response on the screen with the foils in place and generated from the target cannot be from UV radiation and must be due to more penetrating x-rays.

Figure 12:
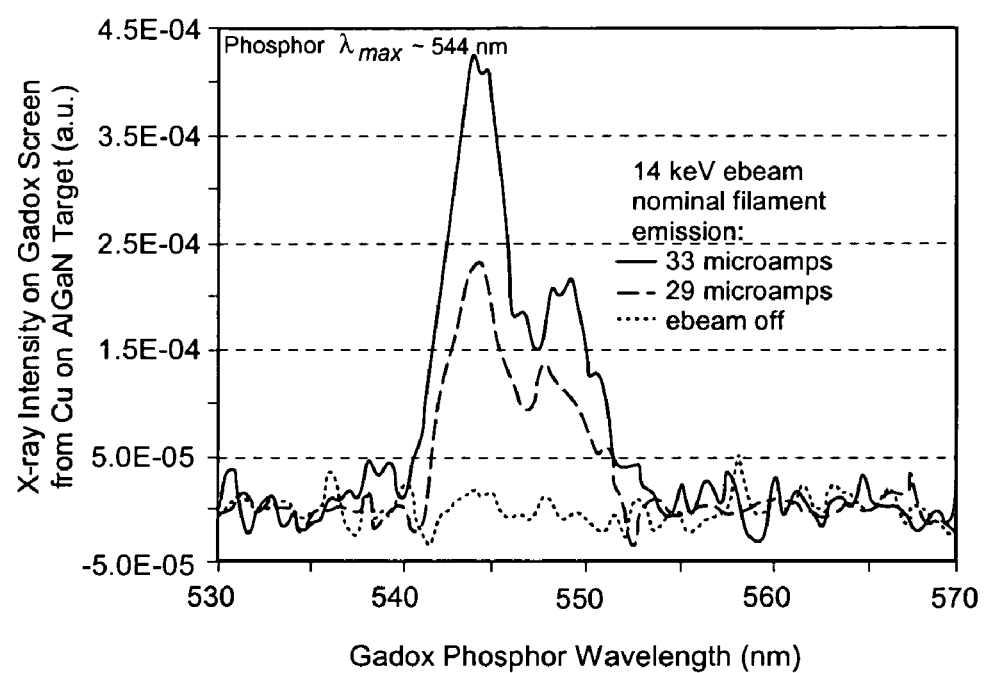
FIG. 12 is a plot of X-ray intensity on a scintillator screen versus phosphor wavelength.

Using identical electron beam conditions as used to measure the CL spectra, a very faint glow was observed on the scintillator screen with the top half brighter than the lower half. When the scintillator response was measured using the spectrometer, it was found that the signal was barely above the noise level. At 10 keV, the maximum filament emission (saturation current) is 24 µA. Therefore, to increase the x-ray signal, the beam conditions were changed to increase the filament emission by raising the beam voltage to 14 kV, thereby increasing the saturation current to 33 µA. The x-ray signals measured at 14 keV and two different filament emission settings are shown in FIG. 12. The spectra shown in FIG. 11 are not x-ray spectra but rather spectra of the green scintillator luminescence, which is proportional to the x-ray intensity striking the screen. As observed in FIG. 12, the x-ray intensity drops by roughly 50% as the nominal filament emission is lowered from 33 µA to 29 µA. This is due to nonlinear variation in the actual current reaching the target. In summary, the data discussed above provides definitive evidence of x-ray emission from the sample.

A number of variations and modifications of the invention can be used. It would be possible to provide for some features of the invention without providing others.

For example in one alternative embodiment, other wavelengths of radiation than UV and/or x-rays are employed.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A decontamination method, comprising:
   (a) contacting a common target with an electron beam to produce a first radiation having a first wavelength band and a second radiation having a second wavelength band;
   (b) contacting a contaminated object with the first radiation; and
   (c) contacting the contaminated object with the second radiation, wherein the contaminated object is contaminated with a microbe, wherein the first radiation kills at least most of the microbes on the surface of the contaminated object but not in an interior region of the object, and wherein the second radiation kills at least most of the microbes in the interior region of the object.

2. The method of claim 1, wherein the first radiation is ultraviolet radiation and the second radiation is x-ray radiation.

3. The method of claim 1, wherein steps (b) and (c) occur simultaneously.

4. The method of claim 1, wherein steps (b) and (c) occur sequentially.

5. The method of claim 1, wherein the target comprises a first material that, when contacted with the electron beam, produces the first radiation and a second material, that, when contacted with the electron beam, produces second radiation.

6. The method of claim 5, wherein the first material comprises at least one passage therethrough and wherein the second material is located in the at least one passage.

7. The method of claim 5, wherein the first material has the formula, $Al_xGa_{1-x}N$, where $0<x<1$ and wherein the second material is a metal.

8. The method of claim 7, wherein the aluminum mole fraction x of the first material, is chosen to allow the most spectral overlap between the first radiation band and the primary band in the UV action spectrum of a particular microbe, resulting in optimal kill of this particular microbe on the surface on the contaminated object.

9. The method of claim 1, wherein the contaminated object is positioned on a surface that is adsorptive of at least a portion of at least one of the first and second radiation and wherein the second radiation has a greater depth of penetration into the object than the first radiation.

10. The method of claim 1, wherein the first radiation has a first center wavelength, or first wavelength of maximum emission in the range of from about 200 to about 400 nm and the second radiation has a second center wavelength, or second wavelength of maximum emission in the range of from about 0.01 to about 10 nm.

11. A decontamination method, comprising:
    (a) contacting a common target with an electron beam to produce a first radiation having a first wavelength band and a second radiation having a second wavelength band;
    (b) contacting a contaminated object with the first radiation; and
    (c) contacting the contaminated object with the second radiation, wherein the contaminated object is contaminated with a microbe, wherein the first and second radiation kills microbes, and wherein the second radiation has a greater depth of penetration into the object than the first radiation.

12. The method of claim 11, wherein the first radiation is ultraviolet radiation and the second radiation is x-ray radiation.

13. The method of claim 11, wherein steps (b) and (c) occur simultaneously.

14. The method of claim 11, wherein steps (b) and (c) occur sequentially.

15. The method of claim 11, wherein the target comprises a first material that, when contacted with the electron beam, produces the first radiation and a second material, that, when contacted with the electron beam, produces second radiation.

16. The method of claim 15, wherein the first material comprises at least one passage therethrough and wherein the second material is located in the at least one passage.

17. The method of claim 15, wherein the first material has the formula, $Al_xGa_{1-x}N$, where $0<x<1$ and wherein the second material is a metal.

18. The method of claim 11, wherein the contaminated object is positioned on a surface that is adsorptive of at least a portion of at least one of the first and second radiation, wherein the first radiation kills at least most of the microbes on the surface of the contaminated object but not in an interior region of the object, and wherein the second radiation kills at least most of the microbes in the interior region of the object.

19. The method of claim 11, wherein the first radiation has a first center wavelength, or first wavelength of maximum emission in the range of from about 200 to about 400 nm and the second radiation has a second center wavelength, or second wavelength of maximum emission in the range of from about 0.01 to about 10 nm.

20. A biological decontamination device, comprising:
    a power source; and
    at least a first source comprising a target that, when contacted with an electron beam, emits both a first radiation having a first wavelength band and a second radiation having a second wavelength band, the at least a first source being powered by the power source, wherein, when a contaminated object is contaminated with a microbe and is contacted with the first and second radiation, the first radiation kills at least most of the microbes on the surface of the contaminated object but not in an interior region of the object and the second radiation kills at least most of the microbes in the interior region of the object.

21. The device of claim 20, wherein the first radiation is ultraviolet radiation and the second radiation is x-ray radiation.

22. The device of claim 20, wherein the target comprises a first material that, when contacted with the electron beam, produces the first radiation and a second material, that, when contacted with the electron beam, produces second radiation.

23. The device of claim 22, wherein the first material comprises at least one passage therethrough and wherein the second material is located in the at least one passage.

24. The device of claim 22, wherein the first material has the formula, $Al_xGa_{1-x}N$, where $0<x<1$ and wherein the second material is a metal.

25. The device of claim 20, further comprising a surface that is adsorptive of at least a portion of at least one of the first and second radiation and wherein the second radiation has a greater depth of penetration into the object than the first radiation.

26. The device of claim 20, wherein the first radiation has a first center wavelength, or first wavelength of maximum emission in the range of from about 200 to about 400 nm and the second radiation has a second center wavelength, or second wavelength of maximum emission in the range of from about 0.01 to about 10 nm.

* * * * *